United States Patent [19]
Yoon

[11] Patent Number: 5,810,851
[45] Date of Patent: Sep. 22, 1998

[54] SUTURE SPRING DEVICE

[76] Inventor: InBae Yoon, 2101 Highland Ridge Dr., Phoenix, Md. 21131

[21] Appl. No.: 610,951

[22] Filed: Mar. 5, 1996

[51] Int. Cl.$^6$ ................................................ A61B 17/04
[52] U.S. Cl. ........................ 606/148; 606/139; 606/144; 606/222
[58] Field of Search .................................. 606/139–142, 606/143, 151, 144, 148, 222; 227/19, 901

[56] References Cited

U.S. PATENT DOCUMENTS

| | | |
|---|---|---|
| 816,026 | 3/1906 | Meier . |
| 1,123,290 | 1/1915 | Von Herff . |
| 2,817,339 | 12/1957 | Sullivan . |
| 3,091,828 | 6/1963 | Soltis . |
| 3,446,212 | 5/1969 | Le Roy . |
| 3,545,444 | 12/1970 | Green . |
| 3,604,425 | 9/1971 | Le Roy . |
| 3,716,058 | 2/1973 | Tanner, Jr. ............................ 606/213 |
| 3,735,762 | 5/1973 | Bryan et al. . |
| 3,870,048 | 3/1975 | Yoon . |
| 3,939,828 | 2/1976 | Mohr et al. . |
| 3,989,049 | 11/1976 | Yoon . |
| 4,217,902 | 8/1980 | March . |
| 4,316,469 | 2/1982 | Kapitanov . |
| 4,337,774 | 7/1982 | Perlin . |
| 4,484,581 | 11/1984 | Martin et al. . |
| 4,485,816 | 12/1984 | Krumme . |
| 4,535,772 | 8/1985 | Sheehan . |
| 4,548,201 | 10/1985 | Yoon . |
| 4,595,007 | 6/1986 | Mericle . |
| 4,637,395 | 1/1987 | Caspar et al. . |
| 4,777,950 | 10/1988 | Kees, Jr. . |
| 4,791,707 | 12/1988 | Tucker . |
| 4,794,927 | 1/1989 | Yoon . |
| 4,869,268 | 9/1989 | Yoon . |
| 4,924,866 | 5/1990 | Yoon . |
| 4,950,258 | 8/1990 | Kawai et al. . |
| 4,961,743 | 10/1990 | Kees, Jr. et al. . |
| 4,979,954 | 12/1990 | Gwathmey et al. . |
| 4,990,152 | 2/1991 | Yoon . |
| 5,007,921 | 4/1991 | Brown . |
| 5,026,379 | 6/1991 | Yoon . |
| 5,026,390 | 6/1991 | Brown . |
| 5,030,224 | 7/1991 | Wright et al. . |
| 5,035,692 | 7/1991 | Lyon et al. . |
| 5,047,047 | 9/1991 | Yoon . |
| 5,053,047 | 10/1991 | Yoon . |
| 5,158,566 | 10/1992 | Pianetti . |
| 5,171,252 | 12/1992 | Friedland . |
| 5,174,276 | 12/1992 | Crockard . |
| 5,207,692 | 5/1993 | Kraus et al. . |
| 5,217,473 | 6/1993 | Yoon . |
| 5,222,976 | 6/1993 | Yoon . |
| 5,226,908 | 7/1993 | Yoon . |
| 5,242,456 | 9/1993 | Nash et al. . |
| 5,309,927 | 5/1994 | Welch . |

(List continued on next page.)

FOREIGN PATENT DOCUMENTS

| | | |
|---|---|---|
| 9505778 | 3/1995 | WIPO . |
| WO96/03925 | 2/1996 | WIPO . |

*Primary Examiner*—Gary Jackson

[57] ABSTRACT

A guide is used to position a suture spring device in anatomical tissue in an elastically deformed, expanded state and is subsequently removed to permit the suture spring device to move from the elastically deformed, expanded state toward a relaxed, contracted state to apply a predetermined compression to the tissue engaged by the device. In one embodiment, the guide includes a hollow, tubular body of coiled configuration defining a plurality of connected coils or rings with a predetermined radius of curvature and a predetermined axial spacing therebetween. The suture spring device includes an elastic body which is of coiled configuration in the contracted state to define a single ring, a portion of a ring or a plurality of connected rings having a radius of curvature and/or axial spacing in the relaxed, contracted state which is smaller than the predetermined radius of curvature and/or axial spacing of the guide so that, when the suture spring device is disposed within the guide, it is maintained in an elastically deformed, expanded state for positioning in anatomical tissue.

37 Claims, 8 Drawing Sheets

U.S. PATENT DOCUMENTS

| | | |
|---|---|---|
| 5,330,503 | 7/1994 | Yoon . |
| 5,334,209 | 8/1994 | Yoon . |
| 5,342,373 | 8/1994 | Stefanchik et al. . |
| 5,439,457 | 8/1995 | Yoon . |
| 5,476,505 | 12/1995 | Limon . |
| 5,486,187 | 1/1996 | Schenck . |
| 5,499,990 | 3/1996 | Schülken et al. . |
| 5,522,822 | 6/1996 | Phelps et al. . |
| 5,582,616 | 12/1996 | Bolduc et al. .......................... 606/143 |

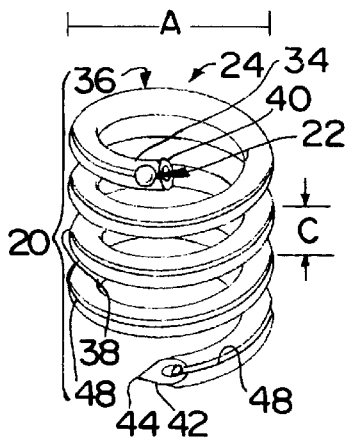
FIG.1
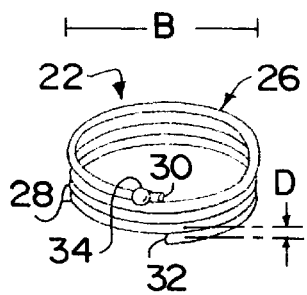
FIG.2
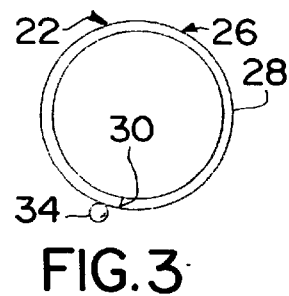
FIG.3
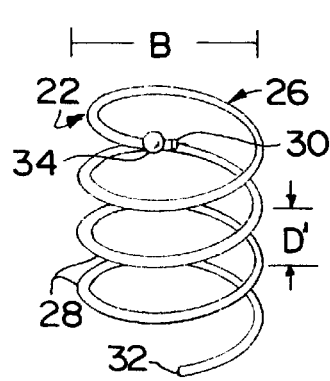
FIG.4
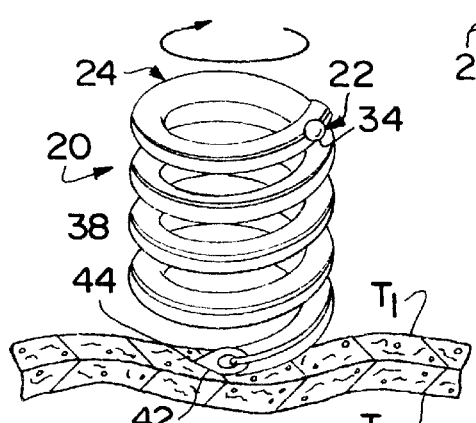
FIG.6
FIG.5
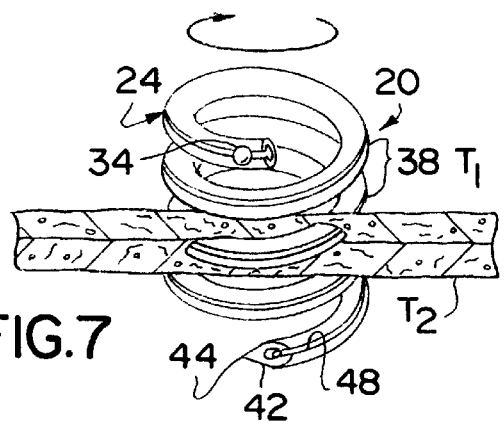
FIG.7
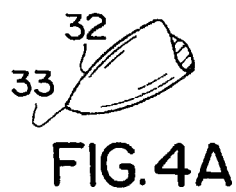
FIG.4A
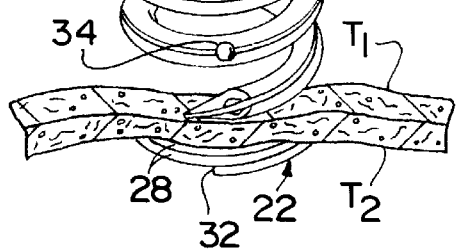
FIG.8
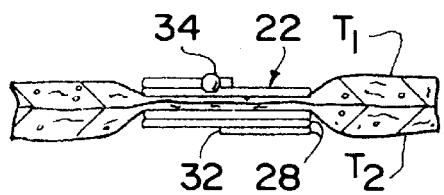
FIG.9

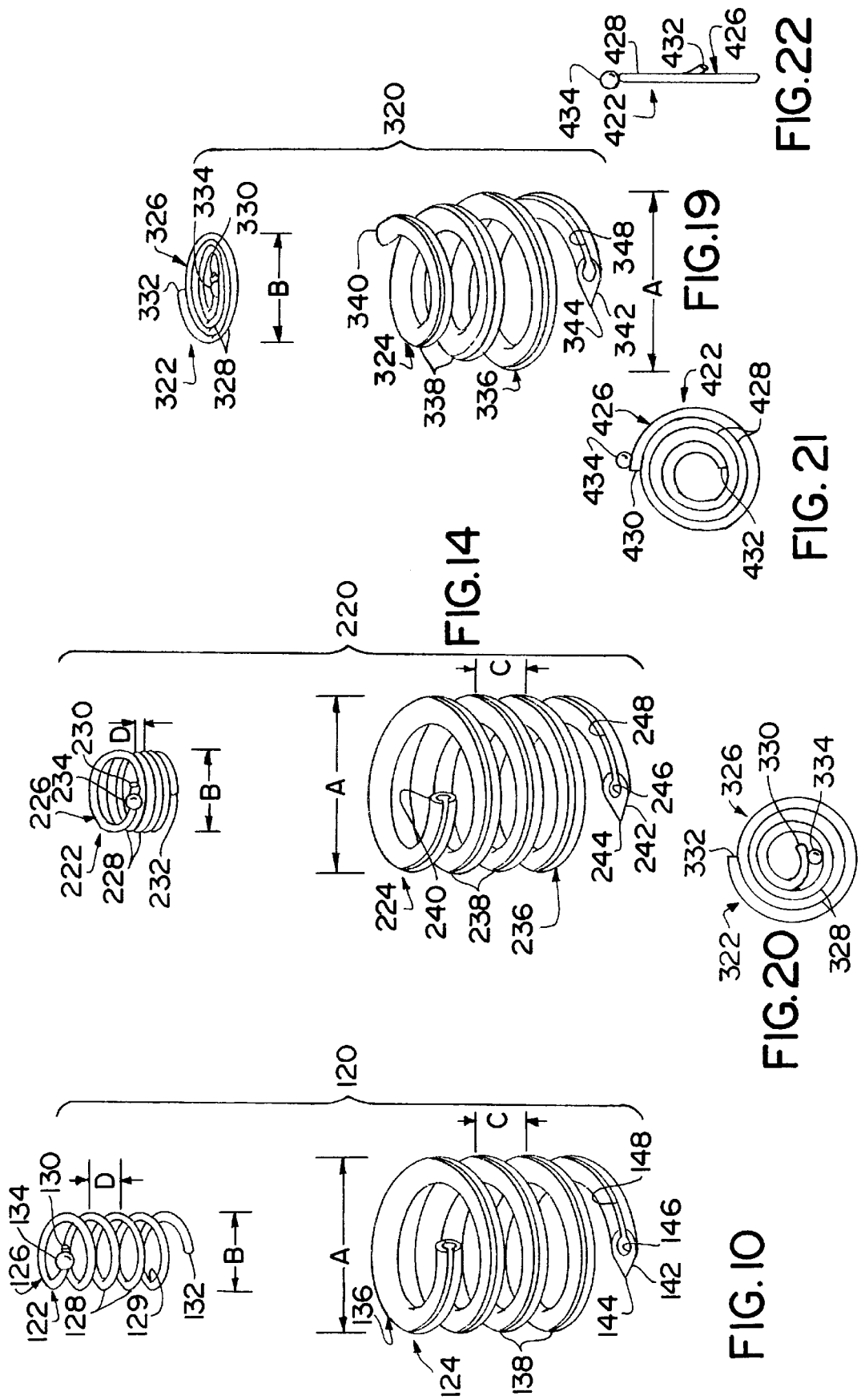

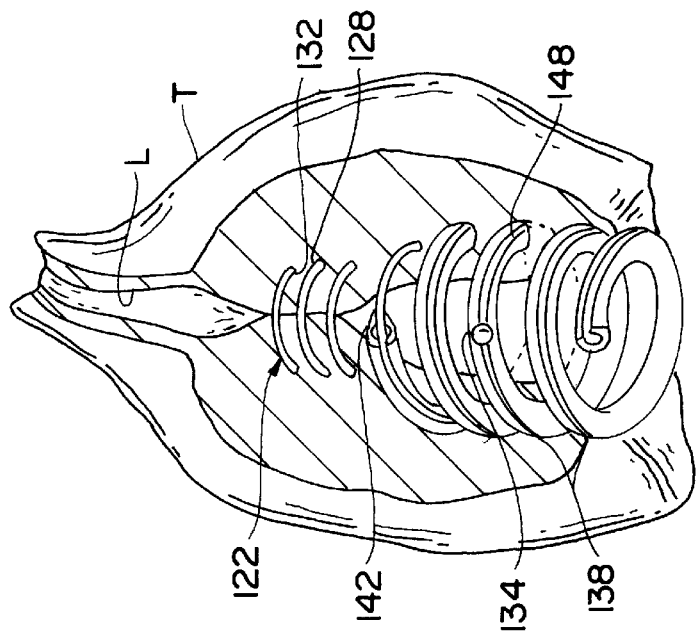
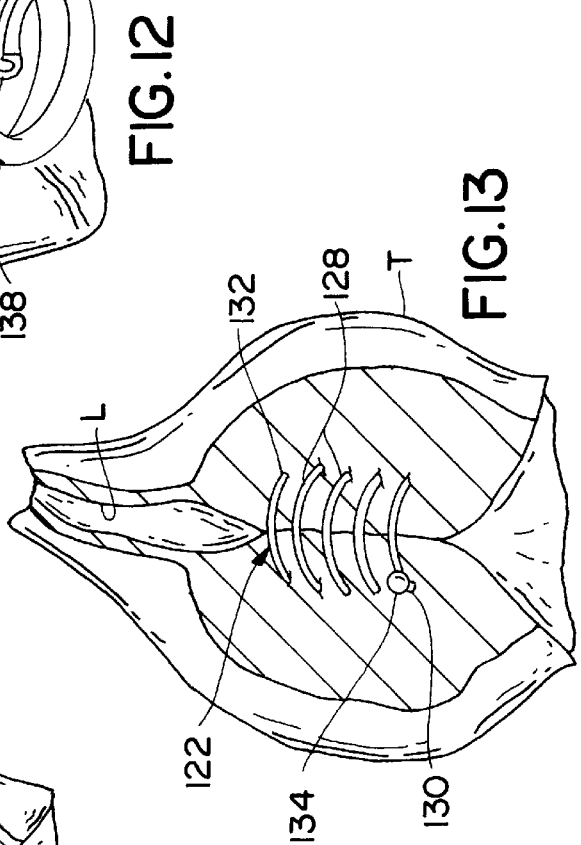
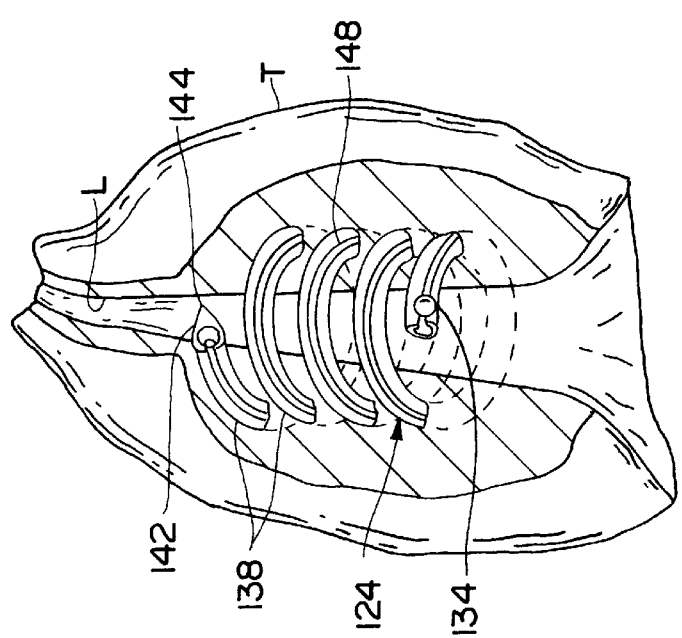

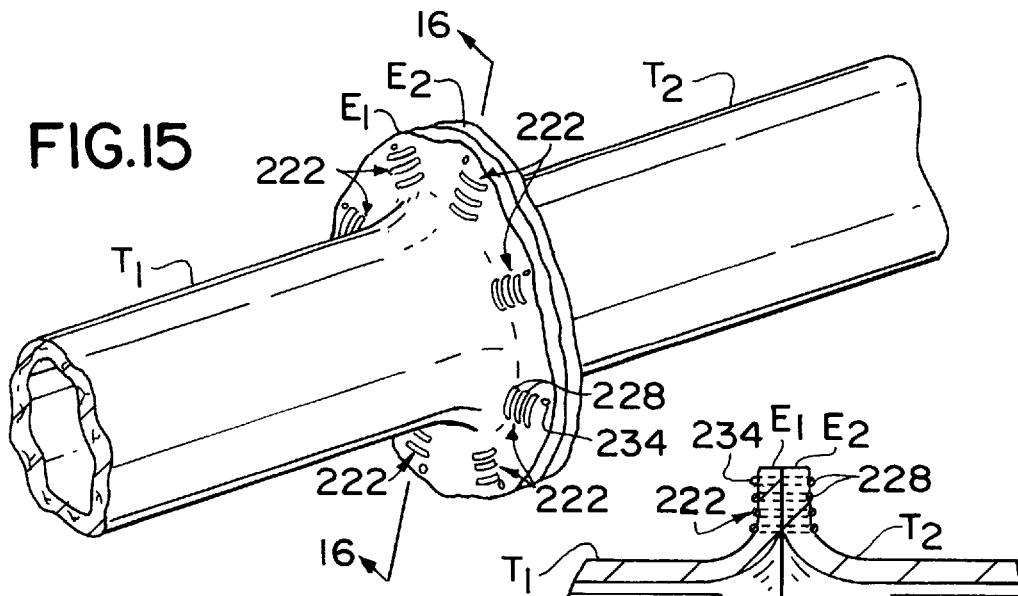
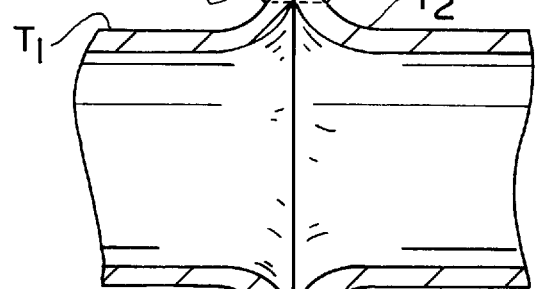
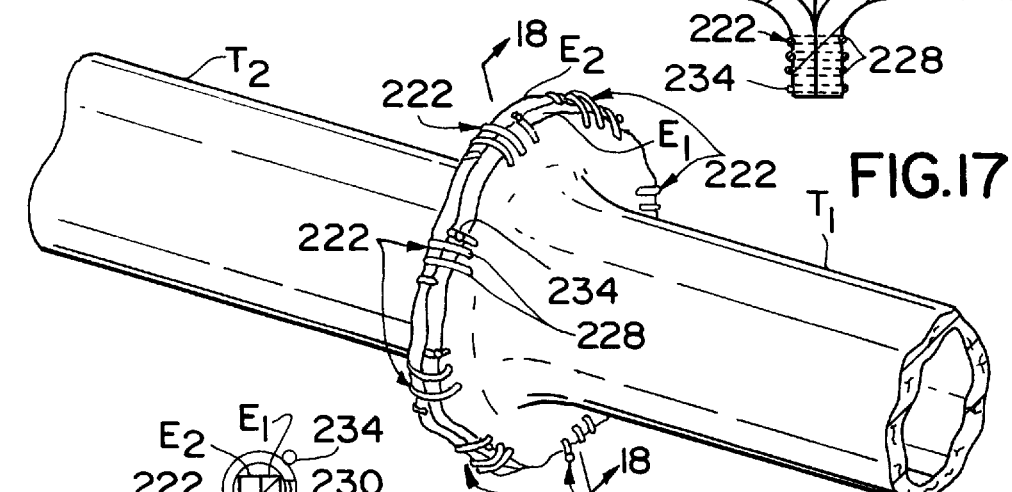
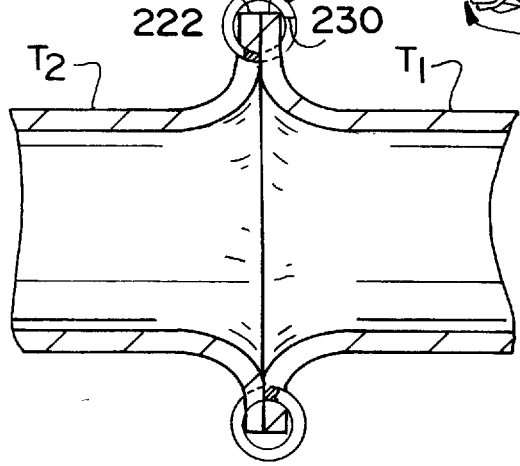

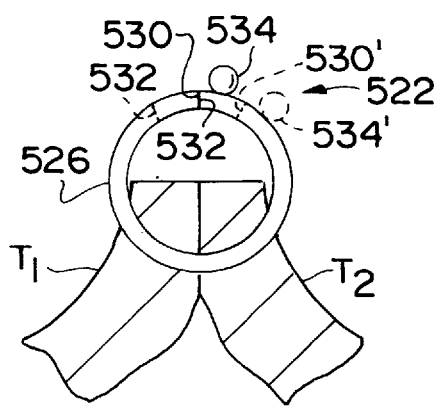
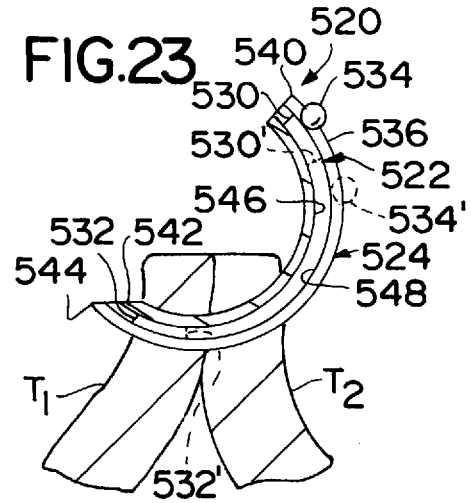
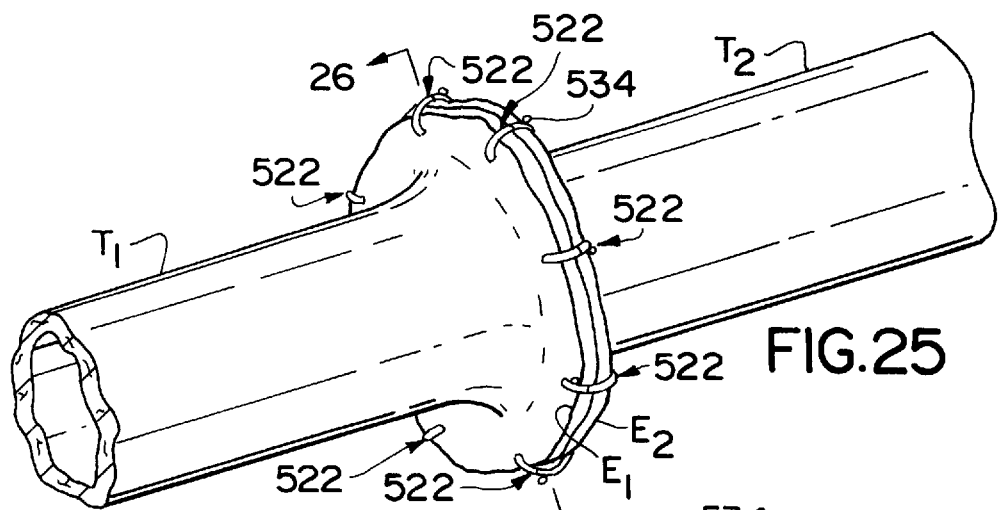
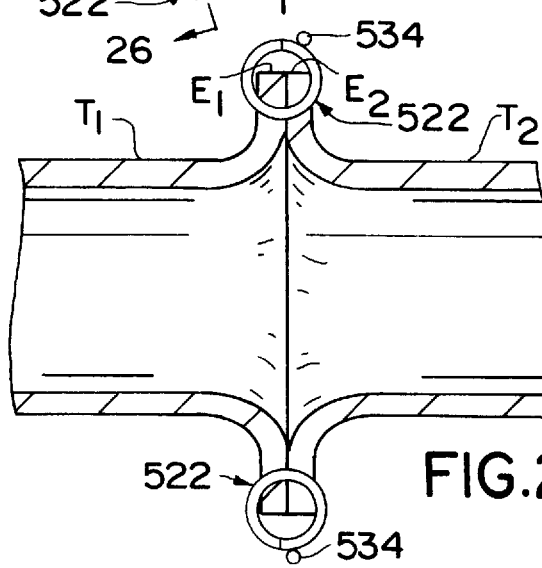

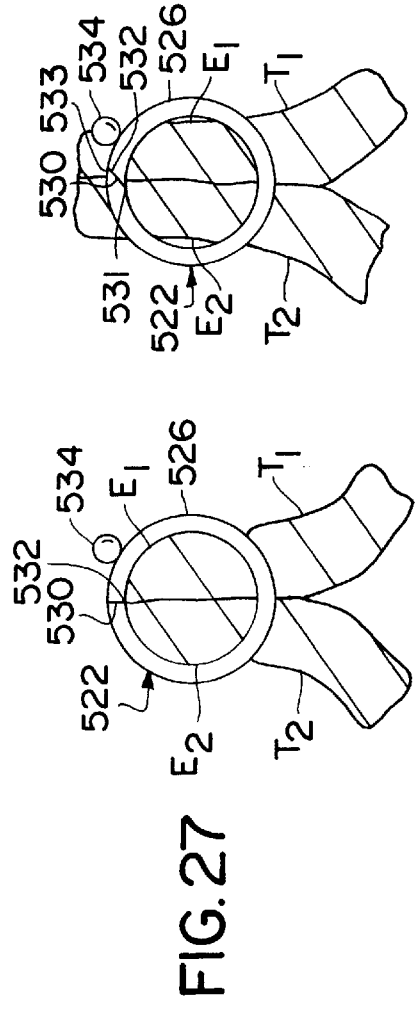
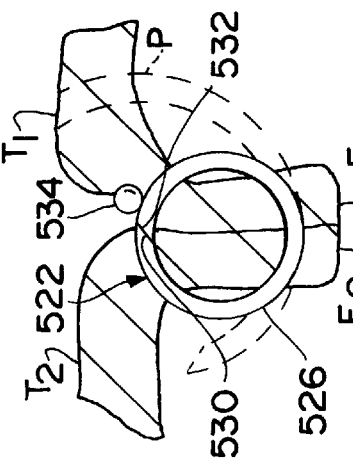
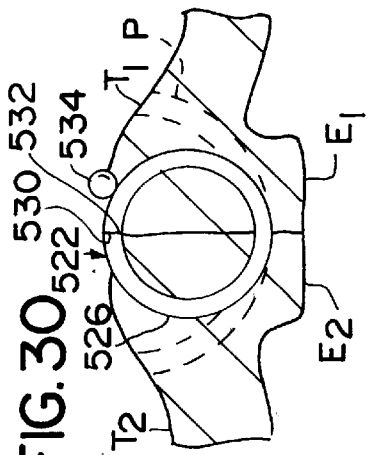
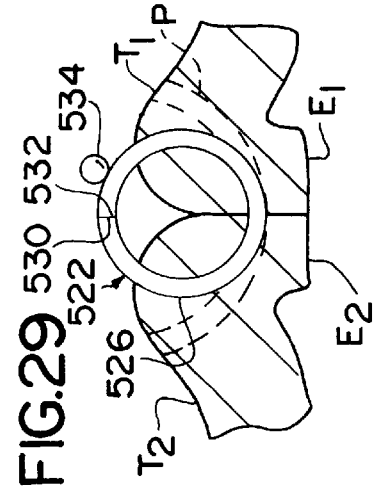
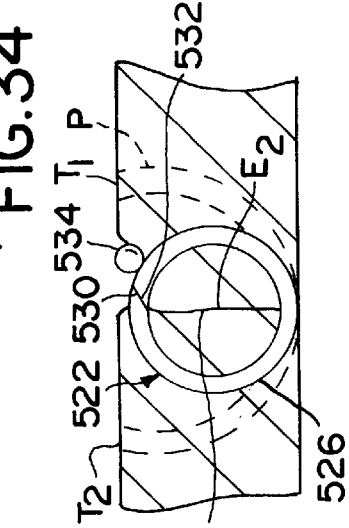
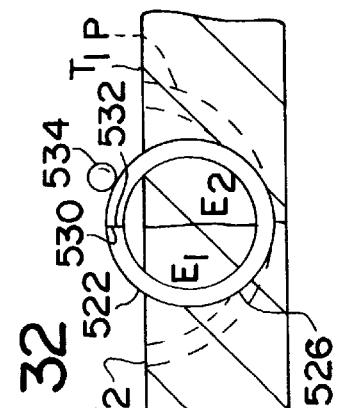

SUTURE SPRING DEVICE

BACKGROUND OF THE INVENTION

1. Field of the Invention

The present invention relates to surgical devices and procedures and, more particularly, to a suture device of coiled configuration formed of an elastic material and methods of suturing anatomical tissue using such a device.

2. Discussion of the Prior Art

Suturing of bodily tissue is a time consuming part of most surgical procedures including both open surgery and endoscopic or minimally invasive surgery. By "open" surgery is meant surgery wherein the surgeon gains access to the surgical site via a relatively large incision, and by "endoscopic" surgery is meant surgery wherein the surgeon gains access to the surgical site via one or more portals through which endoscopes are introduced to view the surgical site and through which various instruments are introduced to the surgical site. There are many common endoscopic surgical procedures, including arthroscopy, laparoscopy (pelviscopy), gastroentroscopy and laryngobronchoscopy, for example.

In the past, suturing was accomplished with the use of a sharp suture needle attached to the end of a length of suture material. Depending on the size of the suture needle and the type of surgery being performed, the suture needle was either grasped manually or with a needle holding instrument and moved to cause a sharp tip of the needle to penetrate and pass through anatomical tissue. When the sharp tip of the needle emerged from the tissue, the body of the needle was released so that the distal end of the body adjacent the tip could be grasped to pull the needle and the suture material attached to the needle through the tissue. Once the suture material was pulled through the tissue, the surgeon tied a knot in the suture material and adjusted the tension on the suture material to accommodate the particular tissue being sutured and to control approximation, occlusion, attachment or other conditions of the tissue. However, the process of tissue penetration and knotting of the suture material can be time consuming and tedious work, particularly when performed in connection with microsurgery and endoscopic surgery, and can unduly prolong the duration of surgery and therefore the period in which the patient is under anesthesia. Nevertheless, endoscopic surgery is preferred over open surgery due to the greatly reduced trauma and wound healing time for the patient and due to concomitant cost savings associated with shorter hospital stays and performing surgery in non-hospital or out-patient surgery sites.

Accordingly, there has been much effort spent to develop techniques for facilitating the suturing normally performed by use of a suture needle and a length of suture material. One technique, exemplified by U.S. Pat. Nos. 3,545,444 to Green and 4,595,007 to Mericle, employs elongated wire sutures formed of ductile materials that are bent into coiled shapes by a curved tip of a suturing instrument. The wire sutures can be bent around tubular structures or through anatomical tissue and will tend to remain in the bent condition to hold the tissue together; however, once bent, the wire sutures will not compress the tubular structures or tissue so that it is necessary to approximate the tubular structures or tissue prior to or concurrent with bending of the sutures.

The use of stapling instruments has also been proposed, as exemplified by U.S. Pat. Nos. 4,979,954 to Gwathmey et al, 5,465,894 to Clark et al, 5,465,895 to Knodel et al, 5,465,896 to Allen et al, 5,467,991 to Tsuruta et al, 5,480,089 to Blewett and 5,486,187 to Schenck; however, stapling instruments typically include separate staple driving and staple forming or anvil portions for positioning on opposite sides of the tissue to be stapled. This requires access to both sides of the tissue and increases the size of the instruments and the portals through which the instruments are passed in endoscopic procedures. Some stapling instruments do not have a separate anvil portion and are thus capable of applying staples from one side of the tissue; however, the staples must still be formed of a ductile material and bent to a final shape by such instruments requiring relatively complex mechanisms which increase the cost of such instruments. Another disadvantage of stapling instruments is that the staples have sharp, tissue penetrating tips which remain in the tissue after the staples have been bent into their final shape.

Other techniques that have been proposed include electrical coagulation, mechanical devices such as clips and clamps, and lasers; however, no alternative technique has yet been well accepted by surgeons to produce the results obtained by suturing and tying. Thus, there is a great need for suturing techniques useful in endoscopic surgery that permit surgeons to suture anatomical tissue in a time efficient, consistent and precise manner.

SUMMARY OF THE INVENTION

Accordingly, it is a primary object of the present invention to overcome the above-mentioned disadvantages of the prior art and to provide an improved suture device and method of suturing anatomical tissue.

Another object of the present invention is to use contraction of a coiled suture device to suture anatomical tissue in a time efficient, consistent and precise manner.

A further object of the present invention is to penetrate anatomical tissue with a guide and to use the guide to position a coiled suture device in the anatomical tissue in an elastically deformed, expanded state so that, when the guide is removed, the coiled suture device will contract to suture the anatomical tissue.

Some of the advantages of the present invention over the prior art are that the process of suturing anatomical tissue can be performed in less time with fewer instruments and with greater consistency in both endoscopic and non-endoscopic procedures, that the suture spring device permits suturing from one side of the anatomical tissue without the need of having to position or reposition instruments on an opposite side of the tissue, that the suture spring device can be made of bioabsorbable and non-bioabsorbable materials, that the suture spring device can be adapted to suture a wide variety of anatomical structures of various shapes and sizes, that the suture spring device can apply a predetermined compressive, approximating force to anatomical tissue in a single direction or multiple directions simultaneously, and that a plurality of suture spring devices can be disposed within a guide and/or carried by a suture device applicator to permit suturing at multiple locations within the body without the need of having to withdraw the guide and/or applicator from the body for reloading.

The present invention is generally characterized in a suture spring device and guide where the suture spring device includes an elastic body of coiled configuration having a relaxed, contracted state and an elastically deformed, expanded state, and the guide is configured to position the suture spring device in anatomical tissue in the elastically deformed, expanded state, the guide being removable from the suture spring device to permit the suture spring device to move resiliently from the expanded state toward the contracted state to apply a compressive, approximating force to anatomical tissue engaged by the coiled body of the device. In one embodiment, the guide includes a hollow, tubular body of coiled configuration defining a plurality of connected coils with a predetermined radius of curvature and a predetermined axial spacing therebetween. The suture spring device includes an elastic body of coiled configuration defining a single ring or a plurality of connected rings having a radius of curvature and/or axial spacing in the relaxed, contracted state which is smaller than the predetermined radius of curvature and/or axial spacing of the guide so that, when the suture spring device is disposed within the guide, it is maintained in an elastically deformed, radially and/or axially expanded state. The guide can be configured with a slot to receive a knob or handle protruding from the suture spring device or, alternatively, the guide can have a solid tubular configuration and a pusher can be provided which is movable through the guide to maintain the suture spring device in the anatomical tissue as the guide is removed.

Yet another aspect of the present invention is generally characterized in a method of suturing anatomical tissue including the steps of positioning a suture spring device of coiled configuration in the anatomical tissue in an elastically deformed, expanded state and allowing the suture spring device to move from the elastically deformed, expanded state toward a relaxed, contracted state within the tissue to apply a compressive, approximating force to the anatomical tissue. In a preferred embodiment, the positioning step includes penetrating the anatomical tissue with a guide and using the guide to position the suture spring device in the anatomical tissue in an expanded state. The guide is then removed to allow the suture spring device to move from the expanded state toward the contracted state.

Still another aspect of the present invention is generally characterized in a suture spring device for use with a guide having an elongate, tubular body of coiled configuration terminating distally in a sharp, tissue penetrating tip, the tubular body defining a plurality of connected rings having a predetermined radius of curvature and a predetermined axial spacing therebetween, and the sharp, tissue penetrating tip allowing the guide to penetrate and pass through anatomical tissue when placed against the tissue and rotated about a longitudinal axis of the guide. In accordance with the present invention, the suture spring device includes an elastic body of coiled configuration having an elastically deformed, expanded state with a radius of curvature and axial spacing to fit inside the coiled tubular body of the guide and a relaxed, contracted state where at least one of a radius of curvature and an axial spacing of the elastic body is smaller than the predetermined radius of curvature and axial spacing of the coiled tubular body of the guide so that, when the guide is removed from anatomical tissue after having been used to penetrate the anatomical tissue and position the suture spring device therein, the suture spring device will remain in the tissue and move from the elastically deformed, expanded state toward the relaxed, contracted state to automatically compress the tissue engaged by the device.

A further aspect of the present invention is generally characterized in a method of suturing anatomical tissue including the steps of penetrating the anatomical tissue with a guide, using the guide to position a suture device in the anatomical tissue in an expanded state, and causing the suture device to move from the expanded state toward a contracted state within the anatomical tissue to apply a predetermined compressive force to the tissue. In a preferred embodiment, the suture device includes an elastic body of coiled configuration in the contracted state and the suture device is caused to move by removing the guide from the suture device to allow the suture device to move resiliently from the expanded state toward the contracted state to apply a predetermined compressive force to the tissue.

Other objects and advantages of the present invention will become apparent from the following description of the preferred embodiments taken in conjunction with the accompanying drawings, wherein like parts in each of the several figures are identified by the same reference numerals or by reference numerals having the same last two digits.

BRIEF DESCRIPTION OF THE DRAWINGS

FIG. 1 is a perspective view of a suture spring device disposed within a guide in an elastically deformed, expanded state according to the present invention.

FIG. 2 is a perspective view of the suture spring device of FIG. 1 in a relaxed, contracted state.

FIG. 3 is a top plan view of the suture spring device shown in FIG. 2.

FIG. 4 is a detail view, in perspective, of the suture spring device of FIG. 2 in the elastically deformed, expanded state.

FIG. 4A is a fragmentary perspective view of a modified distal end for the suture spring device according to the present invention.

FIG. 5 is a top plan view, partly in section, of the suture spring device and guide shown in FIG. 1.

FIGS. 6–9 are perspective views, partly in section, illustrating use of the suture spring device and guide of FIG. 1 to suture anatomical tissue according to the present invention.

FIG. 10 is an exploded perspective view of a modification of the suture spring device and guide according to the present invention.

FIGS. 11–13 are fragmentary perspective views, partly in section, illustrating use of a suture spring device and guide according to the present invention to occlude a tubular anatomical structure.

FIG. 14 is an exploded perspective view of another modification of the suture spring device and guide according to the present invention.

FIGS. 15 and 16 are a fragmentary perspective view and a sectional side view, respectively, illustrating a method of performing anastomosis using a suture spring device according to the present invention.

FIGS. 17 and 18 are a fragmentary perspective view and a sectional side view, respectively, illustrating another method of performing anastomosis using a suture spring device according to the present invention.

FIG. 19 is an exploded perspective view of yet another modification of the suture spring device and guide according to the present invention.

FIG. 20 is a top plan view of the modified suture spring device shown in FIG. 19.

FIG. 21 is a top plan view of another modified suture spring device according to the present invention.

FIG. 22 is a side view, in elevation, of the suture spring device shown in FIG. 21.

FIGS. 23 and 24 are fragmentary side views, partly in section, illustrating a modified suture spring device and guide and a method of suturing using the modified suture spring device and guide. FIGS. 25 and 26 are a fragmentary perspective view and a sectional side view, partly in section, respectively, illustrating a method of performing anastomosis using the suture spring device of FIG. 23.

FIGS. 27 and 28 are fragmentary side views, partly in section, illustrating alternative suture spring device placement when suturing inverted edges of adjacent anatomical structures.

FIGS. 29–31 are fragmentary side views, partly in section, illustrating alternative suture spring device placement when suturing introverted edges of adjacent anatomical structures.

FIGS. 32–34 are fragmentary side views, partly in section, illustrating alternative suture spring device placement when suturing abutting edges of adjacent anatomical structures.

DESCRIPTION OF THE PREFERRED EMBODIMENTS

Figure 35:
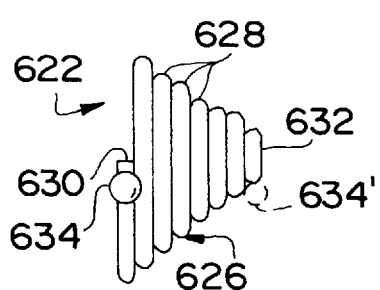
FIGS. 35 and 36 are side and rear views, respectively, of a modified suture spring device according to the present invention.

While the suture spring device of the present invention is described hereinafter as a device for suturing anatomical tissue, where by "suturing" is meant the practice of approximating, occluding or attaching anatomical tissue by joining opposed tissue surfaces or edges together or by attaching devices such as surgical mesh to the tissue, it will be appreciated that the suture spring device can be used to perform other surgical procedures as well. For example, the suture spring device can be used for ligating anatomical tissue, where by "ligating" is meant the practice of tying-off or binding anatomical tissue, for example, as described in my co-pending patent application Ser. No. 08/610,952, filed concurrently herewith, entitled "Method of Ligating Anatomical Tissue With A Suture Spring Device," the disclosure of which is incorporated herein by reference.

A system 20 for suturing anatomical tissue according to the present invention, as illustrated in FIG. 1, includes a suture spring device 22 and a tissue penetrating guide 24 for positioning the suture spring device in anatomical tissue in an elastically deformed, expanded state. Suture spring device 22 is of coiled configuration and, as best seen in FIGS. 2 and 3, the device includes an elongate, wire-like spring body 26 defining a series of connected rings or coils 28 of generally circular configuration, the rings being of like diameter and extending between proximal and distal ends 30 and 32 of the spring body concentric with a longitudinal axis of the device. A knob or handle 34 in the form of a ball is carried on an outer peripheral, convex edge or surface of the spring body near proximal end 30 and extends radially or laterally outward relative to the longitudinal axis of the suture spring device. Body 26 of the suture spring device is circular or round in transverse cross-section with a diameter or gage to permit the suture spring device to be deformed from the relaxed, contracted state shown in FIG. 2, where rings 28 are collapsed against one another in abutting relation, to the expanded state shown in FIG. 4, where the rings are held in axially spaced relation by the guide to define axial, tissue receiving spaces therebetween. The body of the suture spring device is formed of an elastic or resilient material, that is, a material able to recover its original shape or position after having been deformed, so that, when the expanded suture spring device is removed from the guide, the device will relax or tend to move resiliently from the expanded state toward the fully contracted state to compress any anatomical tissue disposed in the axial, tissue receiving spaces between rings. Any medically acceptable bioabsorbable or non-bioabsorbable elastic material can be used for the body of the device including, but not limited to, titanium, nickel-titanium alloys, stainless steel, shape memory alloys such as nitinol and plastics such as nylon. Distal end 32 of the suture spring device is preferably blunt but can be tapered as shown in FIG. 4A to define a sharp, tissue penetrating tip 33 if desired.

Guide 24 includes a tubular body 36 of coiled configuration defining a series of connected rings or coils 38 of generally circular configuration between a proximal end 40 and a distal end 42, the distal end terminating in a sharp, tissue penetrating tip 44. Referring to FIGS. 1–5, it can be seen that rings 38 of the guide body have a predetermined radius of curvature or diameter A about the same as the diameter B of rings 28 of the suture spring device; however, rings 38 of the guide have a predetermined longitudinal or axial spacing C therebetween greater than the axial spacing D between rings 28 of the suture spring device in the relaxed, contracted state so that the suture spring device will be axially but not radially expanded when it is loaded into the guide. Rings 38 of the guide are also hollow to define a lumen 46 through the body of the guide with a slot 48 along an outer peripheral, convex edge of the body communicating between outer surface 50 of the guide and the lumen, the lumen being of sufficient size to receive and hold the body of suture spring device 22 while slot 48 is preferably V-shaped in transverse cross-section and somewhat narrower in width than the diameter of the spring body to allow knob 34 of the suture spring device to slide along the slot while preventing the body of the suture spring device from slipping therethrough. The guide can be made of any suitable medically acceptable material, such as stainless steel, so long as it is configured to have a stiffness suitable for maintaining the suture spring device in an elastically deformed, expanded state.

Suture spring device 22 is normally supplied separate from guide 24 in the relaxed, fully contracted state shown in FIG. 2 with rings 28 collapsed against one another in abutting relation. The suture spring device is preferably loaded into the guide and placed in anatomical tissue using a suture spring device applicator, such as the applicator described in my co-pending application Ser. No. 08/610, 735, filed concurrently herewith, entitled "Suture Spring Device Applicator," the disclosure of which is incorporated herein by reference; however, the suture spring device and guide can be assembled together manually if desired, for example by grasping suture spring device 22 and guide 24, inserting distal end 32 of the suture spring device in open proximal end 40 of the guide and screwing the suture spring device lengthwise into the lumen of the guide in a clockwise direction looking distally. The suture spring device is axially expanded as it is screwed into the guide, that is, rings 28 of the suture spring device are forced away from one another as they are advanced distally through lumen 46 of the guide and are maintained in axially spaced relation within the guide as shown in FIGS. 1 and 4 so that the axial spacing D' between rings 28 of the suture spring device in the elastically deformed, expanded state is about the same as the predetermined axial spacing C between rings 38 of the guide. Knob 34 at the proximal end of the suture spring device is aligned with slot 48 in the guide so that, as the suture spring device is loaded into the guide, the inner portion of the knob immediately adjacent the body of the suture spring device will enter into and slide along the slot while the outer portion of the knob will protrude outwardly of the slot in a radial or lateral direction relative to the longitudinal axis of the guide. In the fully assembled condition, shown in FIG. 1, proximal end 30 of the suture spring device is disposed adjacent proximal end 40 of the guide and distal end 32 of the suture spring device is proximally spaced from the sharp, tissue penetrating tip 44 at the distal end of the guide. It will be appreciated, however, that the suture spring device can occupy less than the total number of coils or rings of the guide in the elastically deformed, expanded state depending upon the length of the guide and the thickness of the tissue to be sutured. Also, more than one suture spring device can be disposed within a single guide if desired.

A first method of suturing anatomical tissue using suture spring device 22 according to the present invention is illustrated in FIGS. 6–9 wherein anatomical tissue to be sutured is shown as a pair of adjacent layers $T_1$ and $T_2$, it being understood that the layers could be adjacent tissue structures, individual layers of a single tissue structure, opposite sides of a single tubular structure, or a surgical device, such as a mesh, laid upon a tissue structure or another surgical device. It will also be understood that a single layer or more than two layers can be sutured with the suture spring device according to the present invention. Suturing is performed by inserting suture spring device 22 through the layers in the elastically deformed, expanded state using guide 24 to penetrate the layers and by then removing the guide from the suture spring device to permit the suture spring device to return towards its relaxed, contracted state. The suture spring device can be inserted through layers $T_1$ and $T_2$ with the guide, as shown in FIG. 6, or the suture spring device can be inserted into the guide after the guide has already penetrated through the layers. In either case, guide 24 is used to penetrate and create a helical path through the layers by orienting the guide at a desired angle relative to proximal layer $T_1$ and pressing the tissue penetrating tip 44 of the guide into the proximal layer while rotating the guide about its longitudinal axis in a clockwise direction, looking distally along the longitudinal axis of the guide, to thread the guide through both layers like a corkscrew. When a suitable number of guide rings 38 are disposed on opposite sides of the layers, as shown in FIG. 7, penetration is ceased, and the suture spring device is released from the guide by unscrewing the guide from the tissue or, in other words, by rotating the guide in the opposite, counterclockwise direction, looking distally. At the same time, the suture spring device is prevented from moving proximally by holding the knob 34 at the proximal end of the suture spring device relatively stationary. Slot 48 in the guide facilitates removal of the guide from the suture spring device by allowing the distal end of the guide to slide past the knob as it is unscrewed. As the guide is unscrewed, rings 28 of the suture spring device are no longer axially restrained by the guide and are thus free to move from their elastically deformed, expanded state toward the relaxed, contracted state as shown in FIG. 9 thereby trapping those portions of layers $T_1$ and $T_2$ disposed between the rings and axially compressing the layers together.

The material and cross-sectional configuration of spring body 26 and the coil diameter and axial spacing of rings 28 in the contracted state are dependent upon the nature of the surgical procedure to be performed, the types of applicator instruments to be used in the procedure and the type of anatomical tissue to be sutured. For example, where a particular suture tension is necessary or desired, the force exerted by the suture spring device when contracting can be controlled by choice of material and by varying the cross-sectional area of the body of the suture spring device. Similarly, the amount of tissue engaged by the suture spring device can be controlled by varying the size of the tissue receiving spaces defined by the suture spring device, that is, by varying the coil diameter and/or the axial spacing between coils in the expanded state.

In the case of a hernia repair, for example, the suture spring device can be used in the manner described above to fasten or tack pieces of surgical mesh to anatomical tissue. When used as a tack, the suture spring device could, for example, include three connected coils or rings formed of spring wire having a cross-sectional diameter or gage of about 0.8 to about 1 mm so that, when the rings are collapsed together in the contracted state, they will have a combined axial length of about 2.5 to about 3 mm. A suitable outer ring diameter B for such a suture spring device could be about 4 to about 4.5 mm, it being understood that the foregoing dimensions are given by way of example only and are not intended to be limiting. In the elastically deformed, expanded state, such a suture spring device could have an axial spacing between rings as much as about 10 times that in the contracted state, or about 10 mm between each ring. Thus, if the combined thickness of the layers being sutured is less than or equal to about 10 mm, for example, the layers will be compressed between a pair of rings with a force approximately equal to the axial spacing between the rings multiplied by the spring constant of the suture spring device. For combined thicknesses greater than the axial spacing between rings, portions of the layers will be compressed between more than one pair of rings of the device.

From the above, it will be appreciated that adjacent structures in the body can be sutured or fastened together with a suture spring device of coiled configuration by inserting the suture spring device through the structures in an elastically deformed, axially expanded state and allowing the suture spring device to contract toward a relaxed state in order to apply an axially compressive load to the portions of each structure disposed between coils of the suture spring device. It will also be appreciated, however, that the rings or coils of such a suture spring device define a longitudinal passage or aperture through the device which can be positioned in or around anatomical tissue in an elastically deformed, radially expanded state and allowed to contract toward a relaxed state in order to apply a radially compressive load to the tissue disposed within the passage. For example, in FIG. 10 a modified suturing system 120 is shown with a suture spring device 122 similar to suture spring device 22 and a guide 124 similar to guide 24 but with a ring diameter A greater than the ring diameter B of the suture spring device in the relaxed, contracted state so that, when the suture spring device is loaded into the guide, it is held in an elastically deformed, radially expanded state. Rings 128 of the suture spring device define a central, tissue receiving aperture or passage 129 of generally circular cross-section concentric with a longitudinal axis of the suture spring device, the passage being diametrically expandable with radial deformation of the suture spring device rings in a laterally outward direction relative to the longitudinal axis. Rings 138 of the guide 124 are spaced at regular axial intervals C approximately equal to the axial spacing D between the coils of the suture spring device in the relaxed, contracted state to minimize axial deformation of the suture spring device in the radially expanded state within the guide.

In use, suture spring device 120 can be assembled and inserted through adjacent layers in the body to suture together or fasten the layers in a manner similar to that described above for suture spring device 20, or the suture spring device 120 can be inserted into the wall of a tubular anatomical structure in a concentric manner with a longitudinal axis of the device aligned with a lumen of the tubular anatomical structure to occlude the lumen by compressing the walls of the tubular anatomical structure together as will be described in greater detail below. If the guide is inserted through layers in the body, tissue disposed in the central aperture or passage defined by the rings will be placed in compression by radial contraction of the suture spring device as the guide is removed but will not be axially compressed to a significant extent because, in the relaxed state, the ring spacing of the suture spring device is not much different than that of the helical path created in the tissue by the guide.

Use of suture spring device 122 to occlude the lumen L of a tubular anatomical structure T is shown in FIGS. 11–13. For purposes of illustration, the suture spring device is shown being applied hysteroscopically at the utero-tubal (UT) junction; it will be understood, however, that the suture spring device can be used to occlude the lumen of any tubular anatomical structure in similar fashion. For such use, guide 122 of the suture spring device will preferably have a ring diameter A greater than the diameter of the lumen so that it can be inserted into the wall of the tubular anatomical structure concentric with the lumen as shown in FIG. 11. The guide can be inserted into the wall with the suture spring device disposed therein in an elastically deformed, radially expanded state or the suture spring device can be inserted into the guide after the guide is already placed in the wall. Once inserted, guide 124 establishes a helical path in the wall of the tubular anatomical structure which the suture spring device will occupy when the guide is removed or withdrawn. Withdrawal of the guide is accomplished by unscrewing the guide from the tissue while at the same time holding the suture spring device stationary, for example by grasping the knob 134 at the proximal end of the suture spring device and holding the knob in a relatively stationary position. As the guide is withdrawn, portions of suture spring device 122 no longer radially constrained within the tubular body of the guide will move toward the relaxed, contracted state as shown in FIG. 12 drawing the wall of the tubular anatomical structure radially inward. When the guide is withdrawn completely from the wall, suture spring device 122 will compress the wall of the tubular anatomical structure radially inward over the entire length of the suture spring device thereby occluding the lumen of the tubular anatomical structure. As discussed previously, the amount of force exerted by the suture spring device will depend on the spring constant of the particular suture spring device being used as well as the extent to which the suture spring device is radially expanded within the guide, it being noted that in the present example, little or no axial force is applied to the structure by the suture spring device since the axial spacing between the rings of the suture spring device is not much different than that between rings of the helical path created by the guide in the wall of the tubular anatomical structure.

Another modification of the suturing system is shown in FIG. 14 wherein the modified system 220 is configured to position a suture spring device 222 in anatomical tissue in an elastically deformed, radially and axially expanded state using a guide 224 similar to guide 24 but with rings 238 having a diameter A greater than the diameter B of the rings 228 of suture spring device 222 in the relaxed, contracted state. Suture spring device 222 is similar to suture spring device 22 but includes an additional ring or coil 228. In the relaxed, contracted state shown in FIG. 14, rings 228 are collapsed against one another in abutting relation so that the axial spacing D from the center of one ring to the next is approximately equal to the wire diameter or gage of the suture spring device body. As mentioned above, rings 238 of guide 224 have a diameter of predetermined dimension greater than the diameter of the rings of the suture spring device in the relaxed, contracted state; and, in addition, the axial spacing C between rings of the guide is greater than the spacing D between rings 228 of the suture spring device in its relaxed, contracted state so that, when the suture spring device is disposed within the guide, rings 228 of the suture spring device are held in an axially and radially expanded state.

Like the suture spring devices described above, suture spring device 222 can be inserted through adjacent layers in the body to suture together or fasten the layers, or the suture spring device can be inserted into the wall of a tubular anatomical structure in a concentric manner with a longitudinal axis of the device aligned with the lumen defined by the tubular anatomical structure to occlude the lumen of the structure. Once guide 224 has penetrated through the layers or into the wall of the tubular anatomical structure, rings 238 of the guide will have established a helical path through the tissue layers or structure which the suture spring device will occupy when the guide is removed. The path created by the guide is initially about the same size as the guide, that is, with a coil diameter and axial spacing greater than that of the suture spring device in a relaxed, contracted state. If the guide was inserted through layers in the body, tissue disposed in the center of the coils will be axially and radially compressed by axial and radial contraction of the suture spring device as the guide is removed; or, if the suture spring device is inserted concentrically into the wall of a tubular anatomical structure such as, for example, a U-T junction, axial and radial contraction of the suture spring device within the path defined in the wall by the guide will tend to draw the wall of the tubular anatomical structure radially inward while axially shortening the structure thereby occluding the lumen defined by the structure. As with the other suture spring devices described herein, the amount of force exerted by the suture spring device as it contracts will depend on the spring constant of the particular suture spring device being used as well as the extent to which the suture spring device is expanded within the guide.

A method of using a suture spring device according to the present invention for performing anastomosis, that is, to connect separate or severed tubular anatomical structures to form a substantially continuous lumen, is illustrated in FIGS. 15 and 16 wherein the tubular anatomical structures $T_1$ and $T_2$ to be connected have abutting, inverted ends $E_1$ and $E_2$, respectively. To connect the tubular anatomical structures, a plurality of suture spring devices, for example suture spring devices 222, are placed in the inverted ends $E_1$ and $E_2$ in radial orientation relative to a longitudinal axis of the tubular anatomical structures at a respective plurality of angularly spaced locations. In order to place the suture spring devices 222, guide 224 is oriented radially or substantially perpendicular to the longitudinal axis of the tubular anatomical structure and distal tip 244 of the guide is moved to penetrate through the inverted ends $E_1$ and $E_2$. The guide is then rotated to cause the penetrating tip of the guide to alternatingly pass through each abutting end as it travels radially inward to create a helical path through the inverted ends which the suture spring device will occupy when the guide is withdrawn. The path created by the guide is initially about the same size as the guide, that is, with a coil diameter and spacing greater than that of the suture spring device in a relaxed, contracted state so that, when the guide is unscrewed from the suture spring device, axial and radial contraction of the suture spring device within the path defined in the tissue by the guide will tend to compress the inverted ends of the tubular organs together thereby connecting the organs. If the ring diameter of the guide is greater than the combined thickness of the inverted ends, diametrically opposed portions of the suture spring device will protrude from opposite sides of the inverted ends as shown. It will be appreciated, however, that the suture spring devices can be completely embedded within the inverted ends by use of a guide having a ring diameter less than the combined thickness of the inverted ends.

Another method of performing anastomosis using a suture spring device according to the present invention is illustrated in FIGS. 17 and 18 wherein a plurality of suture spring devices, for example suture spring devices 222, are placed lengthwise along the peripheral edges of inverted ends $E_1$ and $E_2$ of the organs in substantially tangential orientation relative to the circumference or periphery of the inverted ends at a respective plurality of circumferentially spaced locations about the periphery of the ends. Suture spring devices 222 are placed in the inverted ends $E_1$ and $E_2$ by orienting guide 224 tangentially relative to a circumference of the ends and moving the tip of the guide to penetrate into and through the ends to create a helical path partly within the inverted tissue and partly around the inverted tissue. It will be appreciated, however, that guide 224 can be oriented at any angle relative to the longitudinal axis of the anatomical tubular structures to place suture spring devices 222 in the inverted ends.

Yet another modified suturing system 320, shown in FIG. 19, includes a suture spring device 322 of planar spiral configuration and a generally conical guide 324 formed of a hollow tubular body 336 of coiled configuration. As best seen in FIG. 20, suture spring device 322 includes an elastic body 326 formed of coils or rings 328 having diameters increasing as they approach an outer, distal end 332 of the suture spring device and a knob or handle 334 in the form of a ball carried or formed near a central, proximal end 330 of the suture spring device along an outer peripheral, convex surface of the spring body. Rings 328 of the suture spring device are generally coplanar and, in the relaxed, contracted state shown, the coils are radially collapsed together in abutting relation with the outermost coil of the suture spring device having a diameter B.

Guide 324 includes a plurality of connected coils or rings 338 of increasing diameter in a distal direction, the rings being axially spaced between proximal and distal ends 340 and 342 of the body with a slot 348 formed along an outer peripheral, convex surface of the tubular body to receive the knob of the suture spring device as the suture spring device is loaded into the guide. Distal end 342 of the guide terminates in a sharp, tissue penetrating tip 344. The ring at the proximal end of the guide is of about the same diameter as the outermost ring of the suture spring device, with successive rings of the guide being of progressively larger diameter to radially expand the suture spring device as it is loaded into the guide. One or more of the rings at the distal end of the guide have a predetermined diameter A greater than the diameter B of the outermost coil of the suture spring device in the relaxed, contracted state.

In use, suture spring device 322 is either placed in anatomical tissue with guide 324 or inserted into the guide after the guide has been placed in the tissue. To load the suture spring device into the guide, distal end 332 of the suture spring device is inserted into proximal end 340 of the guide and the suture spring device is rotated relative to the guide, for example, by pushing on knob 334 at the proximal end of the suture spring device. As the suture spring device is advanced distally through the guide, the rings of the suture spring device are elastically deformed by the tubular body of the guide into a radially and axially expanded state where rings of the suture spring device have a radius of curvature and axial spacing similar to that of the guide. Penetration of the tissue with the guide proceeds essentially as described above, with the sharp, tissue penetrating tip 344 of the guide being moved to penetrate the tissue and the guide being rotated to create a path through the tissue for occupation by the suture spring device when the guide is removed. Upon removal of the guide 324 from the tissue, the suture spring device 322 will contract radially and axially toward its relaxed, planar spiral configuration thereby compressing or drawing any tissue disposed within the rings 328 radially inward. For example, if the ring of the guide were inserted into the wall of a tubular anatomical structure concentric with the lumen of the tubular structure, the lumen could be occluded by contraction of the suture spring device toward its relaxed, contracted state.

A modified suture spring device 422, shown in FIGS. 21 and 22, is similar to suture spring device 322 but with a proximal end 430 disposed at the end of the outermost coil or ring and a distal end 432 disposed out of the plane of rings 428 at the center of the spiral. Knob 434 of the suture spring device is carried or formed along an outer peripheral, convex surface of the outermost coil near proximal end 430. In use, suture spring device 422 is loaded into a guide by inserting distal end 432 at the center of the spiral into the opening at the proximal end of the guide and rotating the suture spring device relative to the guide to advance the remainder of the suture spring device through the guide. While providing distal end 432 out of the plane of the coils facilitates insertion, it will be appreciated that the distal end can be arranged coplanar with the coils in the relaxed, contracted state and can then be pushed out of the plane of the coils (e.g., by a force perpendicular to the plane) prior to or during insertion.

Another modified suturing system 520 according to the present invention, as illustrated in FIG. 23, includes a suture spring device 522 in an elastically deformed, expanded state disposed within a guide 524 of partly coiled, curved configuration. Suture spring device 522 is similar to the suture spring devices previously described but with proximal and distal ends 530 and 532 overlapping, abutting or engaging one another in a relaxed, contracted state to form a single loop, coil or ring of generally circular configuration, as shown in FIG. 24. A knob or handle 534 in the form of a ball is carried or formed on an outer peripheral, convex edge or surface of the body of the suture spring device near proximal end 530.

Guide 524 includes a tubular body 536 with a partly coiled or curved shape similar to a standard suture needle but defining a lumen 546 therethrough in communication with a slot 548 extending along an outer, convex edge or surface of the guide between proximal and distal ends 540 and 542, the distal end terminating in a sharp, tissue penetrating tip 544.

In use, guide 524 can be used like a suture needle to penetrate through anatomical tissue, preferably with suture spring device 522 disposed in the guide in the elastically deformed, radially expanded state shown in FIG. 23. For example, when used to suture a pair of anatomical tissue structures together, the sharp, distal tip 544 of the guide is moved to penetrate and pass through the first tissue structure $T_1$ into the second tissue structure $T_2$. The guide is then advanced distally through the second tissue structure until the sharp, tissue penetrating tip 544 of the guide emerges from the second tissue structure, after which the suture spring device 522 is positioned in the tissue and penetration with the guide is discontinued. Guide 524 may then be withdrawn from suture spring device 522 by holding knob 534 of the suture spring device and either retracting the guide in a proximal direction or grasping the distal end of the guide with an instrument such as a needle holder and pulling the guide completely through the tissue in a distal direction as in conventional suturing. Once the guide is removed, suture spring device 522 will no longer be restrained, and proximal and distal ends 530 and 532 of the suture spring device will move toward the relaxed, contracted state shown in FIG. 24 drawing tissue structures $T_1$ and $T_2$ together.

Suture spring device 522 can also be configured as shown by broken lines in FIGS. 23 and 24 to form a partial loop, ring or coil with proximal and distal ends 530' and 532' circumferentially spaced from one another in the relaxed, contracted state so as not to abut, overlap or engage one another.

Use of suture spring device 522 to perform anastomosis of tubular anatomical structures $T_1$ and $T_2$ is illustrated in FIGS. 25 and 26 wherein inverted, abutting ends $E_1$ and $E_2$ of the tubular structures are held together in compression by suture spring devices 522 in the manner described above at a plurality of angularly spaced locations about the periphery of the ends.

In FIGS. 23–26 the point of penetration or entry for guide 524 is chosen to create a shallow path through anatomical structures $T_1$ and $T_2$ less than a ring diameter from an edge of the tissue such that only a portion of the suture spring device 522 is embedded in the tissue when the guide is removed. As a result, when suture spring device 522 moves from the elastically deformed, radially expanded state shown in FIG. 23 toward the relaxed, radially contracted state shown in FIG. 24, proximal and distal ends 530 and 532 of the suture spring device are spaced above the connected edges of the tissue with a gap or clearance therebetween. It will be appreciated, however, that the point of penetration for the guide can be varied to increase or decrease the depth of penetration of the suture spring device. For example, in the case of anatomical tissue structures $T_1$ and $T_2$ shown in FIG. 27, the point of penetration for the guide is spaced inwardly of the connected tissue edges $E_1$ and $E_2$ a distance approximately equal to the ring diameter B of suture spring device 522 to position proximal and distal ends 530 and 532 of the suture spring device immediately adjacent the connected edges of the tissue. This maximizes the depth of penetration of the suture spring device while preventing tissue from becoming trapped or wedged between proximal and distal ends of the suture spring device as the device returns toward the relaxed, contracted state. In FIG. 28, the point of penetration for the guide is spaced from the connected edges $E_1$ and $E_2$ of the anatomical structures $T_1$ and $T_2$ a distance greater than the ring diameter B so that, when the guide is removed, proximal and distal ends 530 and 532 of the suture spring device will be disposed on opposite sides of the tissue. If proximal and distal ends 530 and 532 have sharp, tissue penetrating tips 531 and 533 as shown, the tips can penetrate into the tissue and overlap, abut or engage one another to form a substantially complete loop, ring or coil in the tissue.

FIGS. 29, 30 and 31 illustrate use of the suture spring device 522 to approximate adjacent anatomical tissue structures $T_1$ and $T_2$ with abutting, introverted ends $E_1$ and $E_2$, where by "introverted" is meant being turned outside-in or away from the surgeon. Such a situation can occur, for example, when performing end-to-end anastomosis of separate or severed hollow tubular structures. In FIG. 29, the point of penetration for the guide is chosen to establish a shallow path P through the tissue at the junction of the introverted ends so that proximal and distal ends 530 and 532 of suture spring device 522 will, in the contracted state, protrude outwardly of the tissue to overlap, abut or connect with each other above the junction of the introverted ends with a clearance therebetween. In FIG. 30, the path P established by the guide is somewhat deeper so that proximal and distal ends 530 and 532 of the suture spring device will overlap, abut or connect with each other immediately adjacent the junction of the introverted ends with little or no clearance. The path P established by the guide in FIG. 31 is sufficiently deep to pass completely through the tissue structure $T_1$ on one side of the tissue junction and through introverted ends $E_1$ and $E_2$ so that proximal and distal ends 530 and 532 of the suture spring device will close on opposite sides of ends $E_1$ and $E_2$ and, if provided with sharp, tissue penetrating tips as shown, the ends of the suture spring device will penetrate into the introverted ends of the tissue to overlap, abut or connect with each another forming a substantially complete loop, ring or coil in the tissue.

FIGS. 32, 33 and 34 illustrate use of the suture spring device 522 for approximating anatomical tissue structures $T_1$ and $T_2$ with abutting, non-inverted ends $E_1$ and $E_2$ such as when suturing adjacent anatomical tissue structures or performing real end-to-end anastomosis of severed or separate hollow, tubular anatomical structures with abutting, straight or non-inverted ends. In FIG. 32, the guide is used to make a shallow path P less than a ring diameter below the surface of the tissue so that proximal ends 530 and 532 of suture spring device 522 will, in the contracted state, protrude outwardly of the tissue to overlap, abut or connect with each other above the tissue surface with a clearance. In FIG. 33, the path P established by the guide is about a ring diameter deep so that proximal ends 530 and 532 of the suture spring device 522 overlap, abut or connect with each other immediately adjacent the outer surface of the tissue adjacent the tissue junction. The path P established by the guide in FIG. 34 is more than a ring diameter deep to allow suture spring device 522 to form a loop or ring just beneath the surface of the tissue with proximal and distal ends of the suture spring device being circumferentially spaced from one another in the case of the proximal and distal ends being non-tissue penetrating or overlapping, abutting or connecting with each other in the case of the proximal and distal ends being tissue penetrating as shown.

Figure 36:
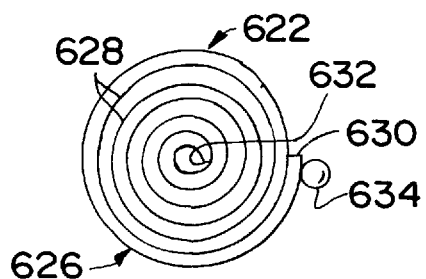

Another modified suture spring device 622 according to the present invention, shown in a relaxed, contracted state in FIGS. 35 and 36, includes a plurality of connected coils or rings 628 of decreasing diameter in a distal direction and a knob or handle 634 in the form of a ball disposed at the proximal end 630 of the suture spring device on an outer, convex surface of a ring. Rings 628 define a generally conical outer surface in the contracted state tapering radially inward from an open base defined by the proximal coil to an open or closed apex defined by the distal coil. Suture spring device 622 is elastically deformable from the relaxed, contracted state shown to a radially and/or axially expanded state using any of the guides shown or described herein. When in the expanded state, the suture spring device 622 can be used to approximate anatomical tissue in any of the ways described above with the apex open or closed.

Suture spring device 622 can also be axially reversed as indicated by broken lines in FIGS. 35 and 36 so that end 630 adjacent the base of the conical suture spring device defines the distal end of the device and end 632 adjacent the apex of the conical suture spring device defines the proximal end of the device. Knob 634' of the reversed suture spring device is mounted adjacent end 632 near the apex of the suture spring device. When placed in anatomical tissue, it will be appreciated that either embodiment of the suture spring device 622 will be less prone to becoming unscrewed because of the variation in coil diameter.

Figure 37:
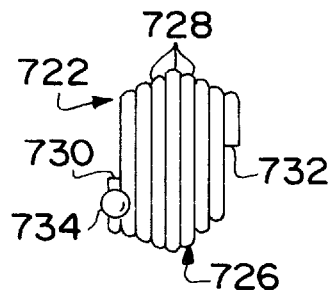
FIGS. 37 and 38 are side and rear views, respectively, of yet another modified suture spring device according to the present invention.
Figure 38:
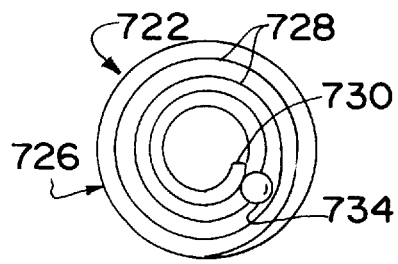

The modified suture spring device 722 shown in a relaxed, contracted state in FIGS. 37 and 38 includes an elastic body 736 of coiled configuration defining a plurality of connected coils or rings 728 that taper radially outward from axially opposed ends to a medial portion or ring of increased diameter. Rings 728 define a generally spherical outer surface in the relaxed, contracted state with one or both of the opposite axial ends of the device being open or closed dependent upon the procedure to be performed. Suture spring device 722 is elastically deformable from the relaxed, contracted state shown to a radially and/or axially expanded state using any of the guides described herein.

Figure 39:
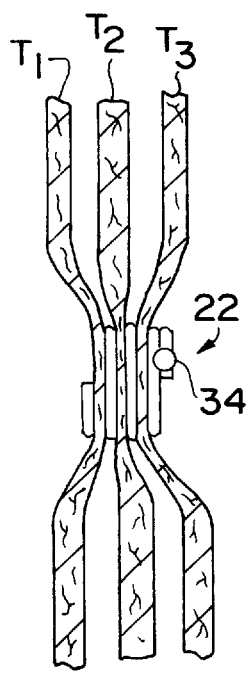
FIG. 39 is a fragmentary side view, partly in section, illustrating use of the suture spring device of FIG. 1 to suture plural tissue layers.
Figure 40:
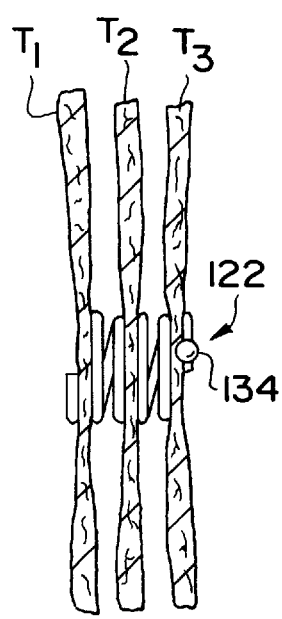
FIG. 40 is a fragmentary side view, partly in section, illustrating use of the suture spring device of FIG. 10 to suture plural tissue layers while maintaining their axial spacing.

As mentioned previously, the suture spring device 22 can be used to approximate any number of layers. For example, in FIG. 39 the suture spring device 22 is used to connect three layers of anatomical tissue and/or surgical devices such as mesh wherein the layers $T_1$, $T_2$ and $T_3$ are compressed along the longitudinal axis of the suture spring device into substantially abutting relation. In FIG. 40, use of the suture spring device 122 to join adjacent layers $T_1$, $T_2$ and $T_3$ in an anatomical body is shown wherein the layers are naturally spaced or dissected to be spaced and it is desired to maintain the spacing between the layers. Suture spring device 122 is inserted through the layers substantially perpendicular to the layers in order to align the axial spaces between the rings of the device with the spaces between layers. The initial spacing between the layers is thus substantially maintained by permitting only radial contraction of the suture spring device when suturing the spaced layers.

Figure 41:
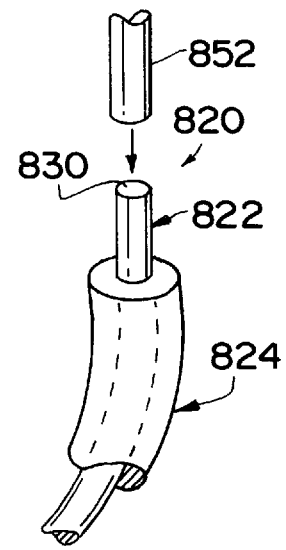
FIG. 41 is a fragmentary perspective view, partly in section, illustrating a modification of the suture spring device and guide according to the present invention.

A further modification of the suturing system according to the present invention is shown in FIG. 41 wherein the modified system 820 includes a suture spring device 822 similar to any of the suture spring devices described herein but without a knob and a tubular guide 824 similar to any of the guides described herein but without a slot. The system 820 further includes a pusher 852 including a flexible rod or finger having a configuration to fit conformably within the lumen of the guide. In use, the suture spring device is inserted into the guide with or without use of the pusher and is held substantially stationary within anatomical tissue by the pusher while the guide is removed by sliding along the pusher in a proximal direction.

Figure 42:
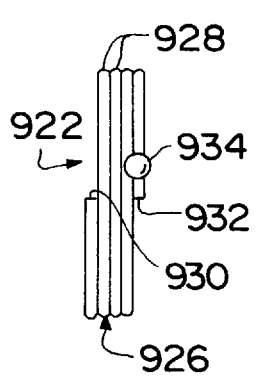
FIG. 42 is a side view, in elevation, of still another modified suture spring device according to the present invention.
Figure 43:
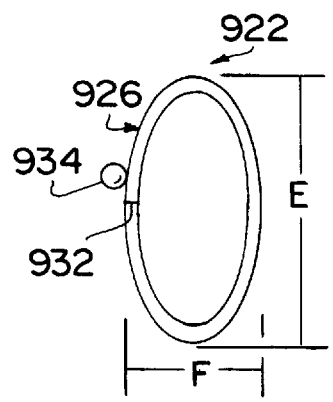
FIG. 43 is a rear view, in elevation, of the suture spring device shown in FIG. 42.

Yet another modified suture spring device 922 according to the present invention, as shown in FIGS. 42 and 43, includes an elastic body 936 of coiled configuration defining a plurality of oval or elliptical coils or rings 928 with a major dimension or length E greater than a minor dimension or width F. Suture spring device 922 can be elastically deformed from the relaxed, contracted state shown to a radially and/or axially expanded state using any of the guides described herein.

Figure 44:
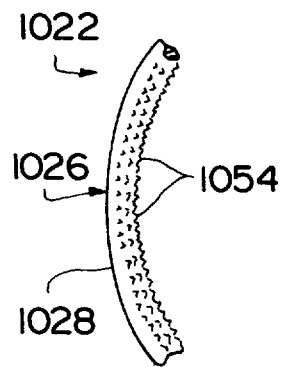
FIG. 44 is a fragmentary rear view, in elevation, illustrating another modification of a suture spring device according to the present invention.

Any of the suture spring devices described herein can be modified as shown in FIG. 44 to include surface features such as tissue engaging teeth 1054 on an inner, concave surface of the rings or on any other part of the exterior surface of the rings. Teeth 1054 can be sharp or rounded or have any configuration to engage anatomical tissue and lock the suture spring device in place relative to the tissue when applied. A suture spring device 1022 provided with surface features such as tissue engaging teeth can be smoothly inserted into anatomical tissue using one of the guides described herein and will be less likely to slip or move relative to the anatomical tissue once applied.

Figure 46:
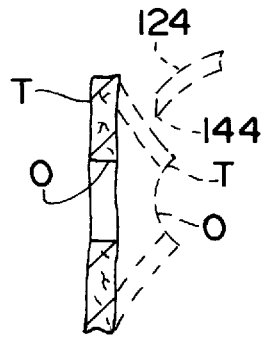
FIGS. 46 and 47 are a side view and a perspective view, respectively, illustrating a method of suturing anatomical tissue adjacent an opening using a suture spring device according to the present invention.
Figure 47:
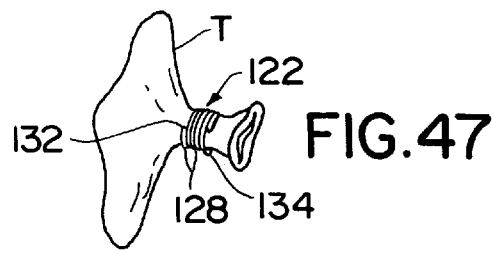

A method of suturing anatomical tissue T adjacent an opening O using a suture spring device according to the present invention is illustrated in FIGS. 46 and 47 wherein tissue edges adjacent the opening are inverted as shown by the broken lines in FIG. 46, for example using a tissue grasping instrument as shown and described in my aforementioned co-pending application entitled "Suture Spring Device Applicator," to permit guide 124 to penetrate through the inverted tissue on opposite sides of the opening and to coil around the inverted edges thereafter with a suture spring device 122 disposed therein in an elastically deformed, radially expanded state. When guide 124 is removed, suture spring device 122 is no longer restrained and will contract radially toward a relaxed, contracted state around the inverted edges as shown in FIG. 47. At least one of the rings 128 of a suture spring device 122 passes through opposed edges of the tissue on opposite sides of the opening to prevent the suture spring device from slipping relative to the inverted tissue.

Figure 45:
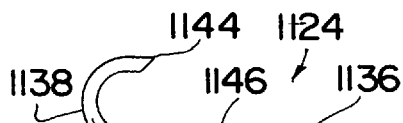
FIG. 45 is a fragmentary side view, partly in section, illustrating a modified guide for use with a suture spring device according to the present invention.

Another modified guide 1124, illustrated in FIG. 45, includes a straight shank 1136 extending from a proximal end of the guide to a curved or partly coiled end 1138 terminating distally at a sharp, tissue penetrating tip 1144. Guide 1124 is tubular and hollow to define a lumen 1146 therethrough for passage of a suture spring device and pusher as described above in connection with the suturing system 820 shown in FIG. 41.

Figure 48:
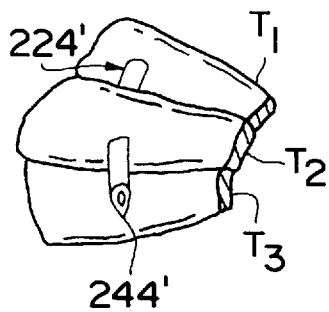
FIGS. 48 and 49 are fragmentary perspective views illustrating a method of suturing anatomical structures using a suture spring device according to the present invention.
Figure 49:
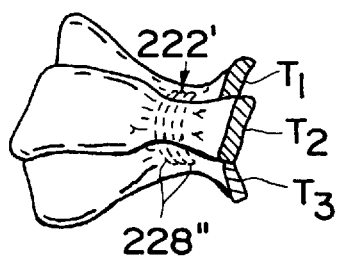

A method of suturing plural anatomical tissue structures $T_1$, $T_2$ and $T_3$ is shown in FIGS. 48 and 49 wherein a hollow tubular guide 224' is passed through the structures in succession using the sharp tissue penetrating tip 224' of the guide to penetrate through the tissue structures. The guide is then removed to allow a suture spring device 222' similar to suture spring device 222 but without a knob to contract axially and radially toward a relaxed, unexpanded state to approximate the anatomical tissue structures as shown in FIG. 49.

From the above, it will be appreciated that adjacent structures in the body can be sutured together with a suture spring device of coiled configuration by inserting the suture spring device through the structures in an elastically deformed, expanded state and causing the suture spring device to move toward a relaxed, contracted state in order to apply a predetermined compressive force to the structures. An axially compressive force can be applied by positioning the structures in the axial space between rings of the suture spring device when the device is in an axially expanded state and by allowing the device to axially contract toward the relaxed state. A radially compressive force can be applied by positioning structures concentrically within the central passage or aperture defined by the rings of the suture spring device when the device is radially expanded and by allowing the coils to contract radially toward the relaxed state around the structures. Also, the suture spring device can be oriented at an oblique angle relative to anatomical tissue to hold the tissue (or surgical devices such as mesh attached to the tissue) in tension.

The suture spring device is preferably positioned in anatomical tissue using a guide having a configuration to hold the suture spring device in the elastically deformed, expanded state. The guide can have a tissue penetrating tip as shown, can be blunt, or the distal end of the suture spring device can be used as a tissue penetrating tip either alone or in combination with the distal end of the guide. The guide can be used to position any type of suture device in or in relation to anatomical tissue by creating a path in or in relation to the tissue which the suture device will occupy when the guide is removed. Hence, in addition to applying suture devices having an elastic body of coiled configuration, the guide can, for example, be used to apply rigid suture devices having substantially the same shape and size as the guide, lengths of filamentary suture material, suture devices formed of shape memory alloys such as nitinol and soft materials that are hardened by application of energy (for example using light provided by fiber optics), and suture devices formed of ductile materials, where by "ductile" is meant having a tendency, once bent, to remain in the bent condition. The guide can also be used like a probe to penetrate and dissect anatomical tissue and to supply energy to tissue or devices as required; and, when the guide is used as a probe, instruments such as the grasping instrument shown in my aforementioned patent application Ser. No. 08/610,735 entitled "Suture Spring Device Applicator" can be used to bring the tissue or device to the probe.

The suture spring device is preferably formed of an elastic body of coiled configuration, where by "elastic" is meant having an ability to recover an original shape or position after having been deformed, and by "coiled" is meant defining a single coil or ring, a portion of a coil or ring or a series of connected coils or rings. Any number of rings or coils can be connected to make up a suture spring device according to the present invention. The rings can be circular, elliptical, polygonal or have any other curved or angular configuration in longitudinal cross-section and, when a device has more than one ring, adjacent rings can be of the same size and shape or of different size and shape depending on the desired tissue engaging shape of the device. For example, the rings can form conical, bi-conical, cylindrical, spherical or pyramidal surfaces when viewed in elevation from the side. The body of the suture spring device can be solid or hollow and can have any configuration in transverse cross-section including, but not limited to, circular, rectangular, elliptical and polygonal configurations. If the body of the suture spring device is hollow, the guide can be disposed within the body to maintain the suture spring device in the elastically deformed, expanded state. In addition, the exterior surface of the body of the suture spring device can be smooth as shown or provided with means for locking the suture device in tissue to prevent forward and/or rearward movement, such as the locking means shown and described in U.S. Pat. No. 5,053,047 to Yoon, the disclosure of which is incorporated herein by reference. When the suture spring device takes the form of a single ring in the relaxed, contracted state, proximal and distal ends of the device can be configured to mate with one another. For example, one end of the suture spring device could be hollow and the other end configured to fit within the hollow end when in the relaxed, contracted state.

The suture spring device can be made of any suitable, medical grade material but is preferably made of an elastic or resilient material, that is, a material able to recover its original position or shape after having been deformed. Furthermore, the spring material can be bioabsorbable or non-bioabsorbable depending on the length of time the tissue is required to be held together. Generally, suitable bioabsorbable materials include thermoplastic polymers such as absorbable polymers and copolymers of, polydioxane, lactide, glycolide and the like. Polyglycolic acid is disclosed in U.S. Pat. Nos. 3,463,158; 3,739,773; and 3,772,420. Suitable polylactic acids are disclosed in U.S. Pat. No. 3,636,956. Examples of absorbable polyesters are shown in U.S. Pat. Nos. 3,225,766 and 3,883,901. Absorbable cellulose glycolic acid ethers are shown in U.S. Pat. No. 2,764,159. Examples of suitable esters of alpha-cyanoacrylic acid are found in U.S. Pat. Nos. 3,527,841; 3,564,078 and 3,759,264.

Once the suture spring device is positioned in or with respect to the tissue, the return of the suture spring device toward the rest position can be enhanced, dependent upon the material from which the suture spring device is constructed, by temperature change and/or by the application of electricity, light or other energy to alter the characteristics of the material.

When the suture spring device is provided with a knob or handle, it can be formed separately from the body of the device and connected thereto by any suitable method, such as by welding, or the knob can be formed integrally with the body as a one-piece unit. The knob can have any shape to protrude from the guide including, but not limited to, the spherical shape shown as well as cylindrical, rectangular, elliptical and conical shapes. Furthermore, the knob can be formed by the body of the device itself by turning the proximal end of the body inwardly or outwardly relative to a longitudinal axis of the device. It will also be appreciated that the handle or knob can be placed anywhere on the spring although it is preferred that the knob be placed near the proximal end of the device so as not to interfere with the penetration of the device through anatomical tissue.

The guide can be made of any suitable medically acceptable material, such as stainless steel, so long as it is configured to have a stiffness suitable for maintaining the suture spring device in the expanded state in anatomical tissue. The guide is preferably of coiled configuration as shown but can also be of straight or angled configuration if desired. When the guide is of coiled configuration, the rings of the guide can be circular, elliptical, polygonal or have any other curved or angular configuration and, when a guide has more than one ring, adjacent rings can be of the same size and shape or of different sizes and shapes depending upon the type of procedure to be performed. The guide preferably includes a tubular body which can have any configuration in transverse cross-section including, but not limited to, circular, elliptical, polygonal and open configurations. Also, the shape of the lumen in transverse cross-section can be different than the shape of the outer surface of the guide in transverse cross-section so that, for example, the outer surface may be circular and the inner surface polygonal or vice versa. Depending upon the manner in which the suture spring device is moved relative to the guide, the guide can be formed with or without a slot. When formed with a slot, the slot will preferably extend from a proximal end of the guide to a distal end of the guide and will communicate between an exterior surface of the guide and an interior lumen or passage. The slot can have tapered or V-shaped sides to accommodate a ball-shaped handle as shown, or the sides of the slot can be straight. Furthermore, although the slot is shown on the outer, convex side of the guide, it can be formed on the inner, concave side or anywhere inbetween or the slot can be made to spiral around the coiled body of the guide.

Any type of force can be used to move the suture spring device relative to the guide including, but not limited to, mechanical forces provided by springs, magnetic forces and/or hydraulic or pneumatic forces. The suture spring device and guide can be held and manipulated using standard needle-holding instruments and forceps, can be grasped directly by hand, or can be provided as part of an applicator instrument specifically designed to apply suture spring devices of the type described herein. For example, the suture spring device could be applied using the applicator shown and described in my aforementioned co-pending patent application Ser. No. 08/610,735, entitled "Suture Spring Device Applicator."

The features of the various embodiments described above can be combined in any manner desired dependent upon the operational requirements of the procedure to be performed and the complexity of the particular design. The material specifications and dimensions of the suture spring device and guide according to the present invention will vary dependent upon the intended use and, as such, it will appreciated that the particular materials and dimensions listed herein are merely exemplary and not meant to be limiting.

Inasmuch as the present invention is subject to many variations, modifications and changes in detail, it is intended that all subject matter discussed above or shown in the accompanying drawings be interpreted as illustrative only and not be taken in a limiting sense.

What is claimed is:

1. In combination, a suture spring device comprising an elastic body of coiled configuration having a relaxed, contracted state and an elastically deformed, expanded state; and
   a guide for holding said suture spring device in said elastically deformed, expanded state for positioning in anatomical tissue, said guide being removable from said suture spring device to permit said suture spring device to move resiliently from said expanded state toward said contracted state to apply a predetermined compressive force to the anatomical tissue.

2. A combination as recited in claim 1 wherein said guide includes a hollow tubular body with proximal and distal ends and said suture spring device is disposed within said hollow tubular body in said elastically deformed, expanded state for positioning in anatomical tissue.

3. A combination as recited in claim 2 wherein said hollow, tubular body of said guide is of coiled configuration.

4. A combination as recited in claim 3 wherein said coiled tubular body of said guide has a predetermined radius of curvature greater than a radius of curvature of said suture spring device in said relaxed, contracted state.

5. A combination as recited in claim 3 wherein said coiled tubular body of said guide includes a plurality of connected rings having a predetermined axial spacing therebetween and said suture spring device includes a plurality of rings having an axial spacing therebetween in said relaxed, contracted state which is less than said predetermined axial spacing between rings of said guide.

6. A combination as recited in claim 3 wherein said coiled tubular body of said guide includes a plurality of connected rings having a predetermined radius of curvature and a predetermined axial spacing therebetween and said suture spring device includes a plurality of rings having a radius of curvature and an axial spacing in said relaxed, contracted state which are less than said predetermined radius of curvature and said axial spacing of said guide rings.

7. A combination as recited in claim 1 wherein said suture spring device includes a plurality of connected rings of decreasing diameter in an axial direction in said relaxed, contracted state.

8. A combination as recited in claim 1 wherein said suture spring device includes a plurality of connected rings which decrease in diameter from a maximum diameter at a medial portion of said device to a minimum diameter at opposite axial ends of said device when said device is in said relaxed, contracted state.

9. A combination as recited in claim 1 wherein said suture spring device includes a plurality of connected, substantially coplanar rings of diminishing diameter in a radial direction in said relaxed, contracted state.

10. A combination as recited in claim 9 wherein a distal end of said suture spring device is disposed at a center of said rings and bent out of the plane of said rings to facilitate insertion into said guide.

11. A combination as recited in claim 1 wherein said suture spring device includes a ring of generally circular configuration with abutting proximal and distal ends in said relaxed, contracted state.

12. A combination as recited in claim 1 wherein said suture spring device includes a proximal end and a distal end and at least one of said proximal and distal ends of said suture spring device includes a tissue penetrating tip.

13. A combination as recited in claim 2 and further comprising a pusher having a flexible finger movable within said hollow, tubular guide body to control the position of said suture spring device relative to said guide.

14. In combination, a suture spring device comprising an elastic body of coiled configuration having a relaxed, contracted state and an elastically deformed, expanded state; and
   a guide for positioning said suture spring device in anatomical tissue in said elastically deformed, expanded state, said guide being removable from said suture spring device to permit said suture spring device to move resiliently from said expanded state toward said contracted state to apply a predetermined compressive force to the anatomical tissue;
   wherein said guide includes a hollow tubular body with proximal and distal ends and said suture spring device is disposed within said hollow tubular body in said elastically deformed, expanded state for positioning in anatomical tissue; and wherein said distal end of said guide includes a tissue penetrating tip.

15. A combination as recited in claim 14 wherein said hollow tubular body is formed with a slot extending between said proximal and distal ends and communicating between interior and exterior surfaces of said hollow tubular body.

16. A combination as recited in claim 15 wherein said slot has a width to prevent said suture spring device from passing therethrough when disposed within said hollow tubular body.

17. A combination as recited in claim 16 wherein said suture spring device includes a knob that extends laterally through said slot when said suture spring device is disposed within said guide.

18. A combination as recited in claim 17 wherein said knob includes a ball disposed adjacent said proximal end of said suture spring device.

19. A combination as recited in claim 15 wherein said hollow, tubular body of said guide has a predetermined radius of curvature and said slot is formed on a convex side of said hollow, tubular body.

20. A method of suturing anatomical tissue comprising the steps of
    positioning a suture spring device of coiled configuration in the anatomical tissue in an elastically deformed, expanded state; and
    causing the suture spring device to move from the elastically deformed, expanded state toward a relaxed, contracted state within the anatomical tissue to apply a predetermined compressive force to the tissue;
    wherein said positioning step includes penetrating the anatomical tissue with a guide and using the guide to hold the suture spring device in the expanded state.

21. A method of suturing anatomical tissue as recited in claim 20 wherein said causing step includes removing the guide from the suture spring device to allow the suture spring device to move resiliently from the elastically deformed, expanded state toward the relaxed, contracted state in the anatomical tissue.

22. A method of suturing anatomical tissue as recited in claim 21 wherein said causing step further includes holding the suture spring device substantially stationary as the guide is removed.

23. A method of suturing anatomical tissue as recited in claim 22 wherein said holding step includes holding a knob extending laterally outward from the suture spring device through a slot in the guide and said removing step includes sliding the guide past the knob in a proximal direction.

24. A method of suturing anatomical tissue as recited in claim 22 wherein said holding step includes advancing a pusher through the guide to abut the suture spring device and said removing step includes sliding the guide over the pusher in a proximal direction.

25. A method of suturing anatomical tissue as recited in claim 20 wherein said positioning step includes placing the elastically deformed, expanded suture spring device in the wall of a tubular anatomical structure concentric with a longitudinal axis of the structure.

26. A method of suturing anatomical tissue as recited in claim 20 wherein said positioning step includes expanding the suture spring device by increasing an axial spacing between rings of the suture spring device and placing the expanded suture spring device in anatomical tissue.

27. A method of suturing anatomical tissue comprising the steps of
    positioning a suture spring device of coiled configuration in the anatomical tissue in an elastically deformed, expanded state; and
    causing the suture spring device to move from the elastically deformed, expanded state toward a relaxed, contracted state within the anatomical tissue to apply a predetermined compressive force to the tissue;
    wherein said positioning step includes expanding the suture spring device by increasing a radius of curvature of the suture spring device and placing the expanded suture spring device in anatomical tissue.

28. A method of suturing anatomical tissue comprising the steps of
    positioning a suture spring device of coiled configuration in the anatomical tissue in an elastically deformed, expanded state; and
    causing the suture spring device to move from the elastically deformed, expanded state toward a relaxed, contracted state within the anatomical tissue to apply a predetermined compressive force to the tissue;
    wherein said positioning step includes expanding the suture spring device by increasing a radius of curvature and an axial spacing between rings of the suture spring device and placing the expanded suture spring device in anatomical tissue.

29. A suture spring device for use with a guide having an elongate, tubular body of coiled configuration terminating distally in a sharp, tissue penetrating tip, the tubular body defining a plurality of connected rings having a predetermined radius of curvature and a predetermined axial spacing therebetween, the sharp, tissue penetrating tip allowing the guide to penetrate and pass through anatomical tissue when the guide is placed against the tissue and rotated about a longitudinal axis of the guide, said suture spring device comprising
    an elastic body of coiled configuration having a relaxed, contracted state where at least one of a radius of curvature and an axial spacing of said elastic body is smaller than the predetermined radius of curvature and axial spacing of the coiled tubular body of the guide, said body having sufficient elasticity to fit inside the coiled tubular body of the guide in an elastically deformed, expanded state so that, when the guide is removed from anatomical tissue after having been used to penetrate the anatomical tissue and position said suture spring device therein, said suture spring device will remain in the tissue and move from said elastically deformed, expanded state toward said relaxed, contracted state to automatically compress the tissue engaged by the device.

30. A suture spring device as recited in claim 29 and further comprising a knob extending laterally outward from said elastic body.

31. A suture spring device as recited in claim 30 wherein said knob is mounted near a proximal end of said elastic body.

32. A suture spring device as recited in claim 29 wherein said elastic body has in said contracted state a radius of curvature about the same as the predetermined radius of curvature of the guide and an axial spacing smaller than the predetermined axial spacing of the guide.

33. A suture spring device as recited in claim 29 wherein said elastic body has in said contracted state a radius of curvature smaller than the predetermined radius of curvature of the guide and an axial spacing about the same as the predetermined axial spacing of the guide.

34. A suture spring device as recited in claim 29 wherein said elastic body has in said contracted state a radius of curvature smaller than the predetermined radius of curvature of the guide and an axial spacing smaller than the predetermined axial spacing of the guide.

35. A suture spring device as recited in claim 29 wherein said elastic body defines a plurality of inwardly spiraled, coplanar rings of diminishing diameter in a radial direction and an end of said elastic body at a center of said rings is angled out of plane relative to said inwardly spiraled rings to facilitate threading of said suture spring device into a hollow guide.

36. A method of suturing anatomical tissue comprising the steps of penetrating the anatomical tissue with a hollow, tubular guide of coiled configuration;

using the guide to position a suture device in the anatomical tissue in an expanded state; and removing the guide from the suture device to cause the suture device to move from the expanded state toward a contracted state within the anatomical tissue to apply a predetermined compressive force to the tissue.

37. A method of suturing anatomical tissue comprising the steps of penetrating the anatomical tissue with a guide;

using the guide to position a suture device in the anatomical tissue in an expanded state; and causing the suture device to move from the expanded state toward a contracted state within the anatomical tissue to apply a predetermined compressive force to the tissue;

wherein the suture device includes an elastic body of coiled configuration in the contracted state and said causing step includes removing the guide from the suture device to allow the suture device to move resiliently from the expanded state toward the contracted state within the anatomical tissue.

* * * * *